United States Patent [19]
Barton et al.

[11] Patent Number: 5,177,308
[45] Date of Patent: Jan. 5, 1993

[54] INSECTICIDAL TOXINS IN PLANTS

[75] Inventors: Kenneth A. Barton, Middleton; Michael J. Miller, Cross Plains, both of Wis.

[73] Assignee: Agracetus, Middleton, Wis.

[21] Appl. No.: 443,425

[22] Filed: Nov. 29, 1989

[51] Int. Cl.$^5$ .................. A01H 5/00; C12N 15/12; C12N 15/82

[52] U.S. Cl. .................. 800/205; 800/DIG. 9; 800/DIG. 43; 435/172.3; 435/320.1; 935/67

[58] Field of Search ........ 800/205, DIG. 9, DIG. 43; 435/172.3, 320.1; 935/67

[56] References Cited

PUBLICATIONS

Barton et al (1987) Plant Physiology 85:1103-1109.
Skinner et al (1989) J. Biol. Chem. 264:2150-2155.
Sagdiev et al (1987) Bivorganicheskaya Khimiya 13(8): 1013-1018.
Darbon et al (1982) Int. J. Peptide Protein Res. 20:320-330.
Ross et al (1988) Comp. Biochem. Physiol. 89C (2): 229-232.
Carbonell, et al (1988) Gene 73: 409-418.
Bougis et al (Nov. 15, 1989) J. Biol. Chem. 264 (32):19259-19265.
Murray et al (Jan. 25, 1989) Nucleic Acids Research 17(2):477-498.
Potrykus (Jun., 1990) Biotechnology 8:535-542.
Dee et al (Apr., 1990) Biotechnology 8:339-342.
Vaeck et al., (Jul. 1987) Nature 328:33-37.
Fischhoff et al (1987) Biotechnology 5:807-813.
Barton, K. A., et al., "*Bacillus thuringiensis* Delta-Endotoxin Expressed in Transgenic *Nicotiana tabacum* Provides Resistance to Lepidopteran Insects," Plant Physiol. 85:1103-1109 (1987).
Grishin, E. V., "Structure and Function of *Buthus eupeus* Scorpion Neurotoxins," Inter. J. Quant. Chem. XIX:291-298 (1981).
Grishin, E. V., et al., "Amino Acid Sequence of Insectotoxin I$_2$ From the Venom of the Central Asian Scorpion *Buthus eupeus*," Bioorganicheskaya Khimiya 5:1285-1294 (1979).
Skinner, W. S., et al., "Purification and Characterization of Two Classes of Neurotoxins from the Funnel Web Spider, *Agelenopsis aperta*," J. Biol. Chem. 264[4]:2150-2155 (1989).
Sagdiev, S. Sh., et al., "Study of the Toxic Components of the Venom of the Cellar Spider *Segestria florentina*," Bioorganicheskaya Khimiya 13[8]:1013-1018 (1987).
Darbon, H., et al., "Covalent Structure of the Insect Toxin of the North African Scorpion *Androctonus australis* hector," Int. J. Peptide Protein Res. 20:320-330 (1982).
Zhdanova, L. N., et al., "Amino Acid Sequence of Insectotoxin I$_1$ From the Venom of the Central Asian Scorpion *Buthus eupeus*," Bioorganicheskaya Khimiya 3[4]: 485-493 (1977).
Ross, D. C., et al., "Toxicity of the Venoms of Two Scorpions (*Androctonus australis* and *Centruroides sculpturatus*) and a Sea Anemone (*Condylactis gigantea*): Acute and Anti-Feeding Actions on the Cotton Bollworm (*Heliothis zea*)," Comp. Biochem. Physiol. 89C[2]:229-232 (1988).
Zlotkin, E., "Pharmacology of Survival: Insect Selective Neurotoxins Derived From Scorpion Venom," Endeavour, New Series, 11[4]:168-174 (1987).
Carbonell, L. F., et al., "Synthesis of a Gene Coating for an Insect-Specific Scorpion Neurotoxin and Attempts to Express It Using Baculovirus Vectors," Gene 73:409-418 (1988).
Ross, D. C., et al., "Peptide Toxins from Arthropod Venoms Disrupt Feeding and Utilization of Diet in the Cotton Bollworm," in Insect Neurochemistry and Neurophysiology, pp. 401-404, Ed. A. B. Borkorec and D. P. Gelman, Humana Press (1986).

*Primary Examiner*—Elizabeth C. Weimar
*Assistant Examiner*—Che Chereskin
*Attorney, Agent, or Firm*—Quarles & Brady

[57] ABSTRACT

Transgenic plants have been created which express an insect-specific toxin from a scorpion. The chimeric inheritable trait produced conditions of toxicity in the plant cells of toxicity to certain insects upon ingestion of plant tissues. The inheritable trait has also been cross-bred to plants transgenic to the *Bacillus thuringiensis* delta-endotoxin to produce plants having two independent insect-specific toxin traits. Insect feeding trails revealed additive toxic effects. A generalized approach for developing other insecticidal toxins as candidates for insertion into transgenic plants is also presented.

2 Claims, 13 Drawing Sheets

Fig. 1

| AmAcid | Codon | Number | /1000 | Fraction |
|---|---|---|---|---|
| Gly | GGG | 160.00 | 10.23 | 0.12 |
| Gly | GGA | 323.00 | 20.66 | 0.25 |
| Gly | GGT | 355.00 | 22.70 | 0.28 |
| Gly | GGC | 445.00 | 28.46 | 0.35 |
| | | | | |
| Glu | GAG | 668.00 | 42.72 | 0.71 |
| Glu | GAA | 278.00 | 17.78 | 0.29 |
| | | | | |
| Asp | GAT | 340.00 | 21.74 | 0.45 |
| Asp | GAC | 422.00 | 26.99 | 0.55 |
| | | | | |
| Val | GTG | 390.00 | 24.94 | 0.33 |
| Val | GTA | 69.00 | 4.41 | 0.06 |
| Val | GTT | 369.00 | 23.60 | 0.32 |
| Val | GTC | 340.00 | 21.74 | 0.29 |
| | | | | |
| Ala | GCG | 214.00 | 13.69 | 0.16 |
| Ala | GCA | 213.00 | 13.62 | 0.15 |
| Ala | GCT | 460.00 | 29.42 | 0.33 |
| Ala | GCC | 490.00 | 31.34 | 0.36 |
| | | | | |
| Lys | AAG | 726.00 | 46.43 | 0.81 |
| Lys | AAA | 168.00 | 10.74 | 0.19 |
| | | | | |
| Asn | AAT | 203.00 | 12.98 | 0.32 |
| Asn | AAC | 430.00 | 27.50 | 0.68 |
| | | | | |
| Met | ATG | 376.00 | 24.05 | 1.00 |
| | | | | |
| Ile | ATA | 69.00 | 4.41 | 0.08 |
| Ile | ATT | 320.00 | 20.46 | 0.39 |
| Ile | ATC | 434.00 | 27.75 | 0.53 |
| | | | | |
| Thr | ACG | 104.00 | 6.65 | 0.13 |
| Thr | ACA | 119.00 | 7.61 | 0.15 |
| Thr | ACT | 232.00 | 14.84 | 0.29 |
| Thr | ACC | 336.00 | 21.49 | 0.42 |
| | | | | |
| Trp | TGG | 232.00 | 14.84 | 1.00 |
| | | | | |
| Cys | TGT | 81.00 | 5.18 | 0.29 |
| Cys | TGC | 200.00 | 12.79 | 0.71 |

| AmAcid | Codon | Number | /1000 | Fraction |
|---|---|---|---|---|
| Tyr | TAT | 122.00 | 7.80 | 0.24 |
| Tyr | TAC | 377.00 | 24.11 | 0.76 |
| | | | | |
| Phe | TTT | 192.00 | 12.28 | 0.28 |
| Phe | TTC | 493.00 | 31.53 | 0.72 |
| | | | | |
| Ser | AGT | 97.00 | 6.20 | 0.09 |
| Ser | AGC | 280.00 | 17.91 | 0.26 |
| Ser | TCG | 111.00 | 7.10 | 0.10 |
| Ser | TCA | 147.00 | 9.40 | 0.14 |
| Ser | TCT | 179.00 | 11.45 | 0.17 |
| Ser | TCC | 250.00 | 15.99 | 0.23 |
| | | | | |
| Arg | AGG | 174.00 | 11.13 | 0.24 |
| Arg | AGA | 119.00 | 7.61 | 0.17 |
| Arg | CGG | 57.00 | 3.65 | 0.08 |
| Arg | CGA | 35.00 | 2.24 | 0.05 |
| Arg | CGT | 145.00 | 9.27 | 0.20 |
| Arg | CGC | 189.00 | 12.09 | 0.26 |
| | | | | |
| Gln | CAG | 325.00 | 20.78 | 0.64 |
| Gln | CAA | 186.00 | 11.89 | 0.36 |
| | | | | |
| His | CAT | 151.00 | 9.66 | 0.43 |
| His | CAC | 197.00 | 12.60 | 0.57 |
| | | | | |
| Leu | TTG | 232.00 | 14.84 | 0.18 |
| Leu | TTA | 36.00 | 2.30 | 0.03 |
| Leu | CTG | 306.00 | 19.57 | 0.24 |
| Leu | CTA | 65.00 | 4.16 | 0.05 |
| Leu | CTT | 279.00 | 17.84 | 0.22 |
| Leu | CTC | 364.00 | 23.28 | 0.28 |
| | | | | |
| Pro | CCG | 222.00 | 14.20 | 0.24 |
| Pro | CCA | 264.00 | 16.88 | 0.29 |
| Pro | CCT | 229.00 | 14.64 | 0.25 |
| Pro | CCC | 200.00 | 12.79 | 0.22 |
| | | | | |
| End | TAG | 11.00 | 0.70 | 0.23 |
| End | TAA | 21.00 | 1.34 | 0.44 |
| End | TGA | 16.00 | 1.02 | 0.33 |

Fig. 2

```
        MM62                    initiation codon 'ATG'

Hind III  BspMI     M  K  K  N  G  Y  A  V  D  S  S
    5'  AGCTTACCTGCGTCACATGAAGAAGAACGGCTACGCCGTGGACAGCAGCG
        3'  ATGGACGCAGTGCACTTCTTCTTGCCGATGCGGCACCTGTCGTCGC
    MM65

G  K  A  P  E  C  L  L  S  N  Y  C  N  N  Q  C  T
        GCAAGGCCCCAGAGTGCCTCCTCAGCAACTACT GCAACAACCAGTGCACC
        CGTTCCGGGGTCTCACGGAGGAGTCGTTGATGA CGTTGTTG GTCACGTGG

MM63  K  V  H  Y  A  D  K  G  Y  C  C  L  L  S  C  Y  C
         AAGGTGCACTACGCCGACAAGGGCTACTGCTGCCTCCTCAGCTGCTACTG
         TTCCACGTGATGCGGGTGTTCCCGATGACGACGGAGGAGTCGACGATGAC
    MM66

F  G  L  N  D  D  K  K  V  L  E  I  S  D  T  R
        CTTCGGCCTCAACGA CGACAAGAAGGTGCTTGAGATCAGCGACACCAGGA
        GAAGCCGGAGTTGCTGCTGTTCT TCCACGAACTCTAGTCGCTGTGGTCCT

K  S  Y  C  D  T  T  I  I  N  *   * Pst I      MM64
        AGAGCTACTGCGACACCACCATCATCAACTAATAGCTGCA 3'
        TCTCGATGACGCTGTGGTGGTAGTAGTTGATTATCG 5'
                                                       MM67
```

Fig. 3

```
  1  GAATTCGAGCTCGCCCTCGAGGAACATGGTGGAGCACGACACTCTCGTCT   50
 51  ACTCCAAGAATATCAAAGATACAGTCTCAGAAGACCAAAGGGCTATTGAG  100
101  ACTTTTCAACAAAGGGTAATATCGGGAAACCTCCTCGGATTCCATTGCCC  150
151  AGCTATCTGTCACTTCATCAAAAGGACAGTAGAAAAGGAAGGTGGCACCT  200
201  ACAAATGCCATCATTGCGATAAAGGAAAGGCTATCGTTCAAGATGCCTCT  250
251  GCCGACAGTGGTCCCAAAGATGGACCCCCACCCACGAGGAGCATCGTGGA  300
301  AAAAGAAGACGTTCCAACCACGTCTTCAAAGCAAGTGGATTGATGTGATA  350
351  TCTCCACTGACGTAAGGGATGACGCACAATCCCACTATCCTTCGCAAGAC  400
401  CCTTCCTCTATATAAGGAAGTTCATTTCATTTGGAGAGGACCAAGCTTTT  450
                                        M  K  K  N  G  Y
451  TATTTTTAATTTTCTTTCAAATACTTCCACCATGAAGAAGAACGGCTACG  500
     A  V  D  S  S  G  K  A  P  E  C  L  L  S  N  Y  C
501  CCGTGGACAGCAGCGGCAAGGCCCCAGAGTGCCTCCTCAGCAACTACTGC  550
     N  N  Q  C  T  K  V  H  Y  A  D  K  G  Y  C  C  L
551  AACAACCAGTGCACCAAGGTGCACTACGCCGACAAGGGCTACTGCTGCCT  600
     L  S  C  Y  C  F  G  L  N  D  D  K  K  V  L  E
601  CCTCAGCTGCTACTGCTTCGGCCTCAACGACGACAAGAAGGTGCTTGAGA  650
     I  S  D  T  R  K  S  Y  C  D  T  T  I  I  N  *  *
651  TCAGCGACACCAGGAAGAGCTACTGCGACACCACCATCATCAACTAATAG  700
701  CTGCAGCAATGGCAACAACGTTGCCCGGATCCCCGGGGATCGTTCAAACA  750
751  TTTGGCAATAAAGTTTCTTAAGATTGAATCCTGTTGCCGGTCTTGCGATG  800
801  ATTATCATATAATTTCTGTTGAATTACGTTAAGCATGTAATAATTAACAT  850
851  GTAATGCATGACGTTATTTATGAGATGGGTTTTTATGATTAGAGTCCCGC  900
901  AATTATACATTTAATACGCGATAGAAAACAAAATATAGCGCGCAAACTAG  950
```

Fig. 5

```
              HindIII  BspMI            M   C   M   P   C   F   T   T   R   P   D   M   A   Q
MM83 ↱    5' AGCTTACCTGCTCGACATGTGCCATGCTTCACCACCCGCCCAGACATGGCCCAGC
MM85 ↰    3'         ATGGACGAGCTGTACACGGTACGAAGTGGTGGGCGGGTCTGTACCGGGTCG
```

```
     Q   C   R   A   C   C       K   G   R   G   K   C   F   G   P   Q   C   L   C   G
    AGTGCCGGCGCCTGCTGC AAAGGCCGGCGCAAATGCTTCGGCCCACAGTGCCTCTGCGGCT
    TCACGGCCGCGGACGACG GCCGTTACGAAGCCGGGTGTCACGGAGACGCCGA
                       GCCGTTACGAAGCCGGGTGTCACGGAGACGCCGA
```

```
     Y   D   *       PstI   BamHI
    ACGACTAATAGCTGCAGG          3'  ↰ MM84
    TGCTGATTATCGACGTCCCCTAG     5'  ↰ MM86
```

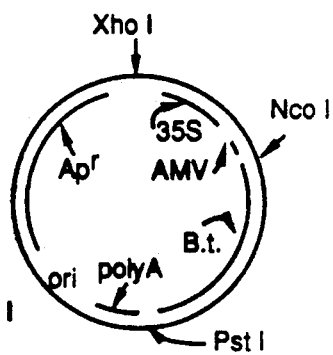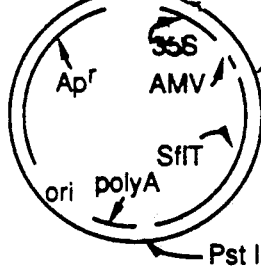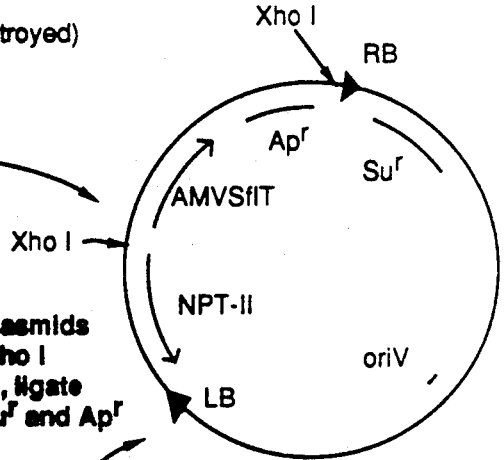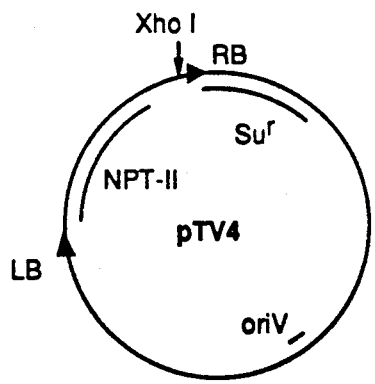
Fig. 13

5,177,308

INSECTICIDAL TOXINS IN PLANTS

FIELD OF THE INVENTION

The present invention relates to the general field of the genetic engineering of plants and relates, in particular, to the genetic engineering of plants to confer to plants a trait of toxicity to specific insect predators.

BACKGROUND OF THE INVENTION

The technology of recombinant DNA manipulation has evolved to a point which now permits the genetic engineering of some higher organisms. In the area of plant technology, it has become possible to genetically engineer many crop plant species, including several commercially important crops. Now that it is possible to transfer exogenous genetic traits into plants, a logical area of investigation is to identify traits which can be added to the plants which will increase their agricultural value. Since the biochemical mechanisms responsible for plant vigor and growth are poorly characterized and understood, and since the technology of the genetic transfer of exogenous traits into plants permits only a relatively few genes to be transferred into plants at any one time, it would appear difficult to envision, given the present state of the art, how dramatic changes in inherent plant growth or vigor characteristics can be obtained through genetic engineering. However, since actual crop yields in normal field situations are often dictated more by predatory factors on the plants, such as disease or insect predation, it is possible to increase the actual yield of crop plants under field conditions not by making the plants grow better, but by adversely effecting the limiting predatory factors which would otherwise decrease the effective yield from the plants. The present techniques for controlling insect predation of crop plants are based on use of synthetic chemical insecticides, which have been an accepted component of the cultivation practices for major agricultural crops, at least in the developed countries, for several decades. Most of the major agricultural chemicals utilized for insecticidal purposes are toxic to a relatively broad spectrum of insect pests and many persist in the environment giving rise to adverse environmental consequences. There have therefore been many efforts to develop pesticidal compounds that are uniquely toxic to specific insects and which also do not persist in the environment.

Biological insecticidal agents can meet several of these criteria For example, there have been several products based on the use of various forms of the delta-endotoxin produced by the soil dwelling microorganism *Bacillus thuringiensis* (*B.t.*) as insecticidal agents. This polypeptide toxin has been found to be specifically toxic to Lepidopteran insects, and has been used for many years commercially as a foliar applied insecticide. It has also recently been found that various forms of the *B.t.* toxin can be toxic to insects, when expressed inside the tissues of plants on which the insects feed. This is the first, and so far only, example of a natural biological insecticide being expressed in the cells of transgenic plants.

It has also been a feature of the history of the use of insecticide in agricultural applications that the insects sometimes become resistant to the applied pesticides. This phenomenon occurs through natural selection of the most insecticidal resistant members of the insect population following continual application of a single insecticidal agent year after year. While no broad spectrum resistance in insects has yet been shown to have developed to a biological toxin, such as the *B.t.* delta-endotoxin, the possibility of the development of such a resistant population must be considered in the long-term planning for the development of insect resistant plants. One way to minimize the possibility of the development of any such insecticidal resistant populations is to impose the insect predators to a regimen of at least two toxins, each of which has an independent mode of activity. The use of two agents, either simultaneously or sequentially imposed on the target populations, dramatically decreases the statistical possibility that resistant insect populations could develop. To be useful as a biological agent to be expressed in plants, such toxins should preferably be polypeptides that can be introduced into plant cells through single gene traits. One place to look for a source for such a toxin is animals which are insect predators.

One class of organism which is able to predate on insects is the scorpion. The scorpion is an Arthropod predator which has relatively poorly developed senses, but which has developed the ability to create a venom which rapidly immobilizes its insect prey, which is otherwise more mobile than the scorpion. The venom of the scorpion serves a dual function, as a defense against possible scorpion predators and to procure its own prey. The venom is therefore composed of a complex cocktail of toxins, many of which are pharmacology active proteins. The activity of the individual proteins from the scorpion toxin has been found to be relatively selective toward specific classes of organisms, such as mammals, insects, or crustaceans.

Several insect-selective neurotoxins have been isolated from scorpions and have been characterized and sequenced. One such neurotoxin, the peptide AaIT which has been isolated from the North African scorpion *Androctonus australis* Hector, is a highly charged polypeptide consisting of seventy amino acids. It has been reported, based on in vitro studies, that the specificity of AaIT peptide is toward a synaptosomal membrane vesicle of insects, and that the protein shows no affinity toward other insect tissues, or for any mammalian, arachnid or crustacean tissues. The AaIT polypeptide binds specifically, reversibly and with high affinity to a single class of non-interactive binding sites on insect neural membranes.

One difficulty incumbent in the genetic engineering of plants to express toxic compounds is that the toxicity of such compounds to plants cells can adversely effect the ability to recover transformed plants. It appears, for example, that plant cells imbued with the trait to produce the full-length amino acid sequence of the B.t. delta endotoxin are negatively selected during present transformation techniques, perhaps due to toxicity of the full-length toxin on the plant cells themselves. It is therefore the case, at least at present, that the in vivo toxicity to plant cells of peptides toxic to insects is not predictable. It is also not possible to predict the toxicity of insect toxins which are normally injected into the insect when such toxins are administered to insects by ingestion.

SUMMARY OF THE INVENTION

The present invention is summarized in that transgenic plants have been created which effectively express in their cells an insect specific toxin of an insect predator in an amount sufficient so as to cause toxicity to selective insects which ingest tissues of the plant.

It is another object of the present invention to provide a method for finding novel strategies for imbuing plants with insect resistance which comprises screening polypeptides produced by insect predators for their effectiveness once inserted into plant cells in imbuing the plants with insect resistant properties.

It is another object of the present invention thus to provide genetically engineered plants which are toxic to insect predators thus lessening the need for artificial agricultural chemicals to protect field crops.

It is yet another object of the present invention to provide alternative insect-selective peptide toxins which can be introduced into plants, in conjunction with B.t. toxins, so as to minimize the possibilities of developing toxin resistant insect populations.

Other objects, advantages, and features of the present invention will become apparent from the following specification when taken in conjunction with the accompanying drawings

BRIEF DESCRITPION OF THE DRAWING

FIG. 1 is a chart of codon usage developed to illustrate codon usage in plant cells and used in construction of the oligonucleotides in the examples of the present invention.

FIG. 2 is a sequence listing of the synthetic coding region for the AaIT toxin and the oligonucleotides used to construct it.

FIG. 3 is a sequence listing of the entire scorpion toxin expression cassette from pAMVST1.

FIG. 5 is a sequence listing of the synthetic coding region for the BeIT1 toxin and the oligonucleotides used to construct it.

FIG. 13 is a schematic illustration of the construction of pTV4AMVSfIT.

DESCRIPTION OF THE INVENTION

Figure 4:
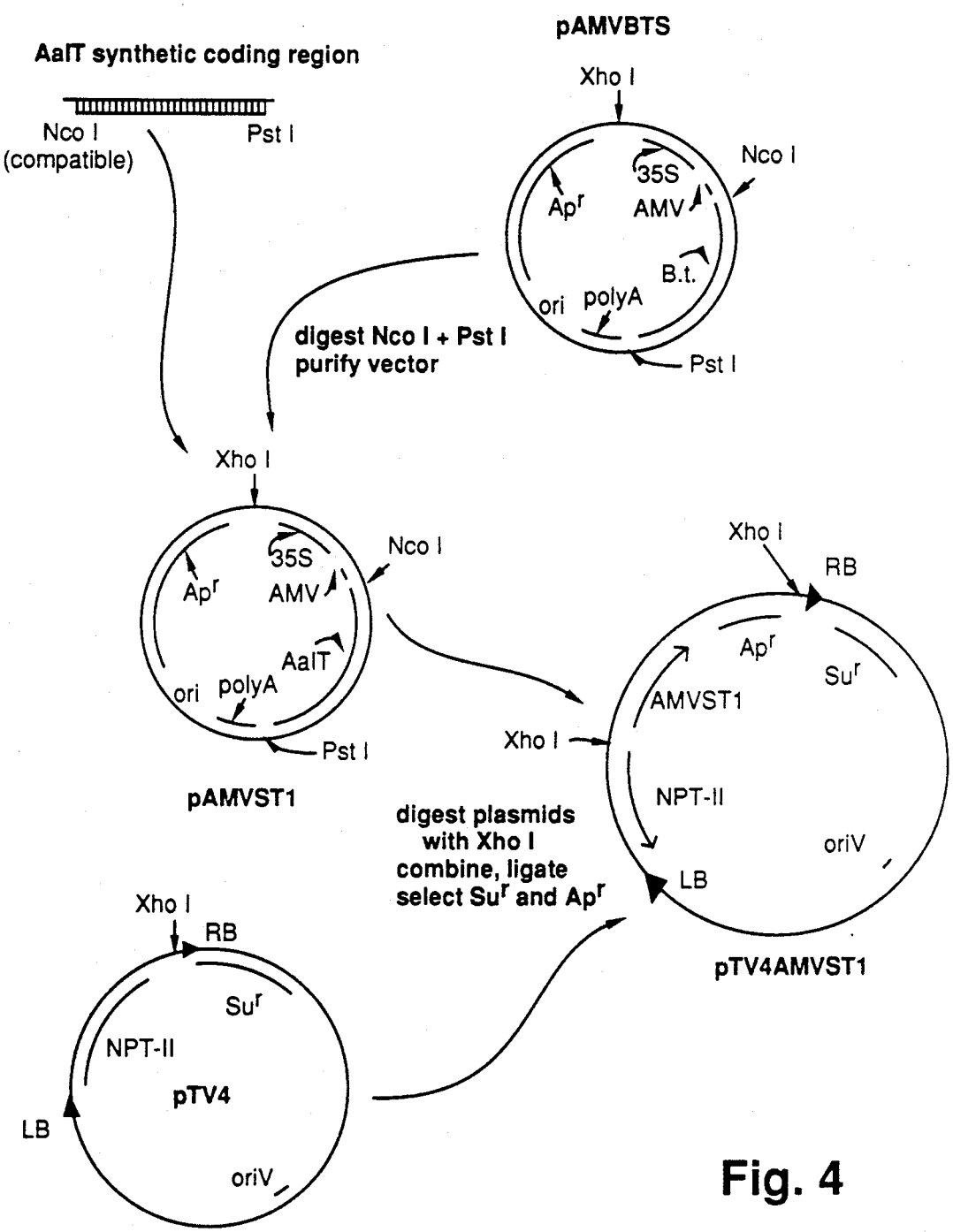
FIG. 4 is a schematic illustration of the construction of the plasmid pTV4AMVST1.

In accordance with the present invention, it has been discovered that a gene for one of the constituents in the venom of an Arthropod insect predator can be synthesized and then genetically engineered into plants to create plants which will have unique and specific toxicity when ingested by certain insect pests. It has been discovered that a protein toxin natively produced by an insect predatory animals such as scorpions and spiders can be successfully expressed in the cells of plants, without damage or visible morphological change to the plant, even while the plant is imbued with a toxicity when ingested by certain insects. Based on these findings, not only are specific genes disclosed herein which have utility for the introduction into various plant species to increase the resistance of the plants to predation by insect pests, but a new class of possible insecticidal agents is disclosed which can be genetically engineered into plants to increase their resistance to predation by insects in general.

One particular toxin which has been discovered here and is described in further detail below is a polypeptide toxin which was discovered as a constituent of the venom produced by a North African scorpion *Androctonus australis*. This toxin has been one which was found to be toxic to insects in both in vitro and in vivo tests. Other toxins illustrated herein are two toxins isolated from a central Asian scorpion *Buthus epeus*, and two toxins isolated from two species of spider. Therefore, from the methodology of the selection and testing from these toxins, and by the logic by which these toxins were isolated and tested, it should be apparent that other similar toxins can be found by similar screening and testing. In particular, the phenomenon of insect toxicity uncovered and found to be effective with the toxin disclosed herein was developed by a rational plan to respond to a perceived need to find other traits which could be introduced into transgenic plants to provide protection against insect predation. It has previously been demonstrated, notably with the toxins produced by the soil dwelling microorganism *Bacillus thuringiensis*, that insecticidal toxins can successfully be produced in plant cells so as to render those plants toxic to insects which ingest them. To find other suitable insecticidal toxins, the inquiry was directed toward predators which rely on insecticidal chemicals likely to have unique toxicity to insects. A wide variety of predators do utilize toxins in preying upon insects, most notably Arthropods such as spiders, scorpions, centipedes and predatory insects such as wasps. The scorpion in particular seemed a preferable candidate from which insecticides could be uncovered. In nature the scorpion is a relatively slow animal with relatively poorly developed visual sense and a poor sense of smell. The scorpion therefore requires a swift acting and potent venom to serve the function of rapidly immobilizing the prey of the scorpion. In addition, significant effort had been expended by others in the isolation, characterization and sequencing of scorpion toxins, which aided in the selection of a particular protein the toxicity of which could be screened. Accordingly, the scorpion toxin represented a class of agents which could be investigated for possible insecticidal toxin activity. Other target predators of insects include any animals which rely on a peptide toxin to either incapacitate or kill their insect prey.

It must be remembered that to be a candidate for genetic insertion into plants, a toxin should ideally meet several constraints. One constraint, at least at present given the level of skill in the art of genetically engineering plants, is that the toxin should preferably be a peptide which can be synthesized by a single gene trait which can be inserted into plant cells. As the technology of plant genetic engineering improves, and the ability to insert larger number of genes becomes developed, it may also be possible to insert genes coding for enzymes which catalyze the synthesis of non-peptide toxins. Another constraint is that the toxin should be selected so as to be relatively specific in its activity.

Many toxins are active broadly against most animals. Such toxins may not be preferred candidates for genetic engineering into plants to be used for human or animal food. However, the developing capacity to construct chimeric genes to express peptides in plants in a tissue-specific manner raises the possibility of using broader spectrum toxins, since it is becoming possible to produce plants which will produce the toxins only in plant tissues that will not be used as animal or human food. Nevertheless, optimal toxin candidate would be a toxin which is uniquely toxic to insects, but which is minimally or not at all toxic to any other classes of animals which might feed on the plants. In particular, it is desired that there be no toxicity to mammals, so that the insertion of the toxin into the cells of plants still results in plants which have unchanged nutritive value to humans or to domestic animals.

Suitable toxins can then be screened both for in vitro and in vivo activity both to determine effectiveness of the toxin and to determine the selectivity of the toxic effect. Such in vitro screening can be done using toxins purified from the animals in question, or using toxins synthesized by gene expression systems used in procaryotic organisms to produce significant quantities of the toxin, or by transgenic introduction into plant cells which can be used in feeding trials on the target insects An example of a suitable toxin, which was isolated from the North African scorpion *Androctonus australis* hector, has been designated AaIT. The insect selective neurotoxin, AaIT, is a polypeptide consisting of 70 amino acids. It has been previously suggested that the 8 cystine residues in AaIT contribute to 4 disulphide bridges of the mature AaIT protein which combine to give the protein a unique secondary structure which contributes toward the selectivity of the toxin toward insects, relative to other scorpion toxins which are active toward vertebrate life forms. Darbon et al., *Intern. J. Peptide Protein Res.*, 20 p. 320 (1982). Previous work by others has indicated that the AaIT peptide has specific affinity toward the synaptosomal membrane vesicles of insects and has little or no affinity for non-innervated insect tissues, or for tissues of other animal forms, such as mammals, arachnids, or crustaceans. It has been reported that the AaIT polypeptide binds specifically, reversibly, and with a high affinity to a single class of non-interactive binding sites on the insect neural membrane. Others have previously demonstrated that the AaIT peptide has toxicity against various insects when applied topically, when injected, or when ingested at high doses by certain insect larvae. Similar research has been reported establishing the toxicity and specificity of two toxins, designated BeITI and BeIT2 isolated from the Asian scorpion *Buthus epeus*.

Once a toxin, such as AaIT, has been selected, it is then necessary to prepare a chimeric expression cassette suitable for expressing the peptide in the cells of target plants. There are a number of ways in which such a chimeric expression cassette can be constructed, as is known to those of ordinary skill in the art. At a minimum, the construction of such an expression cassette requires a promoter which initiates transcription of a downstream coding region in the cells of plants. Downstream of the coding region in the plant it is required that there be a translation or transcription terminator, such as a polyadenylation sequence, several examples of which are known to be useful in the genetic engineering of plants. Between the promoter and the coding region, it is also possible to use a 5' non-coding translational enhancer sequence. One such preferred sequence which has been effectively utilized is the 5' non-coding sequence from the alfalfa mosaic virus coat protein gene.

The coding sequence itself can be created in a number of ways. One strategy for the creation of such a coding sequence would be to isolate the mRNA of the toxin gene, as expressed in the cells of the insect predator, and then to create a cDNA coding region corresponding to the coding sequence in the organism which is the native host to the toxin. However, since it has also been found that certain coding sequences work better than others in the expression of proteins in plant cells, a preferred strategy would be to discover the amino acid sequence of the peptide toxin, and then to synthesize a coding region customized so as to maximize the expression of the toxin protein in plant cells. If the amino acid sequence is of a reasonable size, it is well within the scope of reasonable skill in the art at the present time to synthesize such coding regions, as has been done here. In order to optimize the translational efficiency of such systems, it is possible to analyze the pattern of codon usage by plant genes which are normally expressed at abundant levels. By examining the frequency of codon usage by efficiently or very actively expressing natural plant genes, it is possible to determine which codons are, in essence, preferred within the translational systems normally present in plant cells. It is therefore possible to construct a synthetic coding region for any peptide which includes, as the codon for each amino acid in the peptide, the codon which is most preferred by plant cells, at least in the native genes most actively expressed in those plant cells. Using such preferred usage codons, it is possible to construct a protein coding sequence which will result in a significantly enhanced level of translational efficiency compared to what would be achieved by taking the coding sequence directly from the organism which natively produces the toxin peptide.

Once the chimeric plant expression cassette is constructed, it is then necessary to transform the constructed gene into plant cells. There exist at present several mechanisms for the insertion of foreign genes into plants. One method, such as utilized here, involves a plant pathogenic bacterium known as *Agrobacterium tumefaciens*. Wild-type Agrobacterium tumefaciens harbors a plasmid, referred to as the Ti plasmid, which has the native ability to transfer a portion of its DNA, referred to as T-DNA, into the genomic DNA of infected plant cells. By removing the genes which code for tumorous activity normally contained within the T-DNA of an Agrobacterium, and by substituting for the Ti plasmid with a foreign expression cassette synthetically constructed, it is possible to use the natural genetic engineering ability of *Agrobacterium tumefaciens* to transform any desired foreign gene into plant cells. Other techniques for genetic engineering of plants have also been developed, which obviate some of the disadvantages of Agrobacterium transformation, and provide the theoretical ability to transform many, if not all, plant species. Such techniques include the electroporation and regeneration of plant protoplasts, the direct injection of naked DNA into plant flowers, and, most notably, the newly developed technique of particle-mediated acceleration plant transformation. In accordance with the techniques of genetically engineering plants using particle-mediated plant transformation, naked DNA containing copies of a plant expression cassette is coated onto extremely small carrier particles.

The carrier particles can then be physically accelerated by an explosive force, such as achieved through an electric shock discharge, into the living cells of plant tissue. Tissue types which can be readily transformed through particle-mediated transformation techniques include the growing meristem of plants, plant embryos, and plant germ cells such as pollen.

It is envisioned that any of the above plant transformation techniques may be used within the scope of the present invention. Based on the experience to date in the genetic engineering of plants, there appears to be little difference in the expression of genes, once inserted into plant cells, attributable to the method of plant transformation itself. Since some transformation techniques can result in more than one copy being inserted, and since the site of foreign DNA insertion appears to be random using any technique, the activity of the foreign gene inserted into plant cells seems more dependent on the expression characteristics of the individual inserted genes resulting both from the chimeric control regions (promoters, polyadenylation regions, enhancers, etc.) and from the influence of indigenous plant DNA adjacent the chimeric insert, and by copy number, rather than by the technique of inserting the genes into plants.

The process of creating insect resistant plants in accordance with this method cannot be considered complete once a coding sequence for the foreign gene has been inserted into plant cells and the plants regenerated into whole plants. It is then necessary to test the transgenic plants thus created through appropriate biological assays by insect feeding. Only by empirically testing the toxicity of such plants to insects themselves can it be truly determined if the desired toxicity has been obtained.

EXAMPLE 1

Toxin Expression Cassette

The synthesis of the expression cassette for the expression of the scorpion toxin AaIT in plant cells was commenced with the alteration of a previously constructed plant expression cassette constructed for the expression of the *B.t.* delta-endotoxin in plant cells. This plasmid, which had previously been designated pAMVBTS, included a promoter sequence derived from the cauliflower mosaic virus 35S gene (CaMV 35S), followed by a 5' non-coding region which had been synthetically constructed to correspond to the 5' non-coding region from the alfalfa mosaic virus coat protein, which had previously been found to enhance the efficient expression of synthetic genes in plant tissues. Following the 5' non-coding translational enhancer was a shortened toxin coding sequence for the B.t. delta-endotoxin, followed by convenient cleavage sites for restriction enzymes including a Pst I site, followed by a polyadenylation region derived from the nopaline synthase gene derived from the Ti plasmid of *Agrobacterium tumefaciens*. Also on the plasmid pAMVBTS, reading in the opposite direction, was a selectible marker for ampicillin resistance constructed to be expressive in the cells of procaryotic hosts. The plasmid pAMVBTS has previously been deposited with the American Type Culture Collection, Rockville, Md., as Accession No. 53637 deposited June 24, 1987. Details of this plasmid may be found in Barton et al., *Plant Physiol.*, 85, pp. 1103-1109 (1987) and published PCT patent application WO 89/04868 published Jun. 1, 1989, the disclosure of both documents being hereby incorporated herein by reference.

The seventy amino acid protein sequence for the AaIT insect toxin polypeptides had previously been reported by Darbon et al., *Int. J. Pep. Res.*, 20, pp. 320-330 (1982). Since the intent was to construct an expression cassette for optimal efficiency in expressing the protein in plant cells, as opposed to arthropod cells, the coding region of the toxin was not cloned from its native host, but it was instead synthesized so as to enhance the translational effectiveness of the protein coding region in plants. An artificial toxin coding DNA sequence was therefore first derived based on the published amino acid sequence. To develop such a synthetic coding sequence, reference was had to a table, previously developed, listing the frequency of expression of the codons utilized by native plant genes in the expressions of efficiently produced native plant proteins. FIG. 1 herewith contains the amino acid codon usage frequency table which had been ascertained by the investigators here based on publicly available sequence data on sequenced plant genes which had been determined to be efficiently and highly expressed in plant cells. Thus for each amino acid position in the desired peptide, a codon was selected representing the most popular codon used in native plant cells to express that particular amino acid in native plant genes. The preferred codons for each amino acid are indicated by outlines in FIG. 1. Based on this rule of preferred codon usage, a 210 base pair synthetic nucleotide sequence to code for the same 70 amino acid polypeptide produced in the scorpion was derived. In order to synthesize a DNA sequence of that length, six overlapping and homologous synthetic oligonucleotides were created corresponding to the overall sequence which was desired. The overall protein coding sequence with the six oligonucleotides, designated MM62 through MM67, is shown in FIG. 2. The total expression cassette for the AaIT toxin in plant cells, derived from the plasmid pAMVBTS by substituting the AaIT peptide coding region for the *B.t.* region, with the AaIT toxin coding region extending from nucleotides 482 through 694, is shown in FIG. 3, and is designated pAMVST1.

To construct the expression cassette for pAMVST1, the six overlapping synthetic oligonucleotides were initially annealed in pairs of two to form a double-stranded molecule. The initial center pair (MM63 and MM66) was then kinased to add phosphate groups to each 5' end. The three double stranded oligonucleotides were ligated and then inserted into a plasmid pUC18 which had been previously digested Hind III and PST I. The resulting plasmid, designated pUCST1, was sequenced to ensure that the insert was the desired sequence as illustrated in FIG. 2.

The synthetic DNA sequence was designed to incorporate a 5' restriction enzyme site for the enzyme BspMI immediately adjacent to the initiating methionine codon (ATG) of the insect toxin coding region as noted in FIG. 2. The plasmid pUCSTI was first digested with Pst I to release the 3' end of the insect toxin coding region, and also to destroy the BspMI site located within the polylinker derived from pUC18. The linear DNA fragment thus created was then digested with BspMI to release the 5' end of the coding region with a "CATG" sticky end, which would be compatible in ligation with an Nco I restriction site, a site which was conveniently available in the plasmid pAMVBTS.

The plasmid pAMVBTS was then digested with Nco I and Pst I, and the expression cassette portion of the vector isolated from the BTS coding region. The synthetic scorpion toxin coding region was then ligated into the vector. This process is illustrated in FIG. 4. The resulting plasmid, designated pAMVST1, incorporates the plant expression cassette in its entirety derived from the plasmid pAMVBTS. The expression cassette thus consists of a CaMV 35S transcriptional promoter, a 5' non-coding translational enhancer having a sequence similar to that of the alfalfa mosaic virus coat protein mRNA non-coding region, a synthetic DNA fragment encoding the protein sequence for the AaIT insect toxin, and the polyadenylation region for nopaline synthase. A selectible marker of ampicillin resistance was also included in the plasmid pAMVST1 for selection in bacteria.

To enable the transformation of plant cells with Agrobacterium, the expression cassette pAMVAaIT was cointegrated into the *Agrobacterium tumefaciens* binary vector pTV4 as described in Barton et al., and WO 89/04868, both incorporated by reference above, with reference to the plasmid pAMVBTSH. The deposited plasmid pTV4AMVBTSH, ATCC accession No. 53636 is a convenient source of plasmid pTV4 by digesting the cointegrate plasmid pTV4AMVBTSH with Xho I, by ligating the digestion products to reclose the two resultant plasmids pTV4 and pAMVBTS, and by transformation into *E. coli* with selection for sulfadiazene resistance. A miniprep will confirm the isolation of pTV4. The same procedure, with selection for ampicillin resistance, can be used to derive pAMVBTS for use as an expression vector in plants.

To cointegrate pAMVST1 into pTV4, both plasmids were digested with Xho I, the linearized DNAs were combined and religated. The product was transformed into *E. coli* and selected for both sulfadiazene and ampicillin resistance, and then confirmed by miniprep analysis.

In order to do in vitro toxicity studies using the toxin, supplies of AaIT toxin were obtained from Sigma.

Plant Transformations

The plasmid pAMVST1 was cointegrated into the binary vector pTV4, and conjugated into an Agrobacterium strain EHA101 as described by Barton et al., supra. Seeds of tobacco (*Nicotiana tabacum* variety Havana 425) were surface sterilized and germinated on MS medium so that aseptically grown leaves and stems could be used for plant transformation procedures. The aseptically grown tobacco tissues were inoculated with Agrobacterium containing the transformation vectors, and the plants were regenerated following selection for kanamycin-resistant transformants in a manner well known to those skilled in the art. The resulting transformant plants, designated as R0 plants, were analyzed for appropriate toxin DNA, RNA, and protein components within the cells of those plants as described below.

Toxicity Studies

The first toxicity studies conducted with the transgenic plants were conducted with tobacco hornworm (*Manduca sexta*), which had been purchased as eggs from Carolina Biological Supply. Initial feedings of tobacco hornworms on R0 plants derived from the regenerates failed to demonstrate any ascertainable toxicity to the insects.

In order to verify that the insensitivity of the feeding insects was due to ineffectiveness of the toxin rather than a failure of the transformation techniques, RNA screens were then conducted on approximately 40 R0 plants which had been created. This screen was done by slot-blot hybridizations conducted on RNA from each of the transformants. Northern gels were run to determine the integrity of the hybridizing RNA in the transformants. The procedures used for such slot-blots and Northern gels are discussed in Barton et al., supra. Several of the R0 plants which had the highest levels of hybridizing RNA were then self-pollinated to provide seed for R1 seedling analysis. One particular plant was initially identified to have a very active transcription of the gene encoding for the AaIT protein. This plant, designated plant T2636, was determined to have approximately 0.001% of its total mRNA homologous to the AaIT probes, while other regenerates expressed at various lower levels. Such variation and activity of gene expression from heterologous genes inserted into plants is quite common following Agrobacterium transformation, or other known techniques for inserting genes into plants. The most highly expressing plants were then assayed further with the principal focus being on plant 2636 and the progeny created from its self-pollination. The transcript analysis of the RNA from these plants showed hybridizing mRNA of the expected size of 530 nucleotides including the poly-A tail. Measurement of relative levels of the transcript from the AaIT and the APH-II (Kanamycin resistance) coding regions showed a consistent 10-fold difference in concentration of AaIT RNA compared to the APH-II RNA, which might be due to the difference in promoter regions (the stronger CAMV 35S promoter on the AaIT gene versus the nopaline synthase promoter on the APH-II gene) but this is not certain.

Figure 9C:
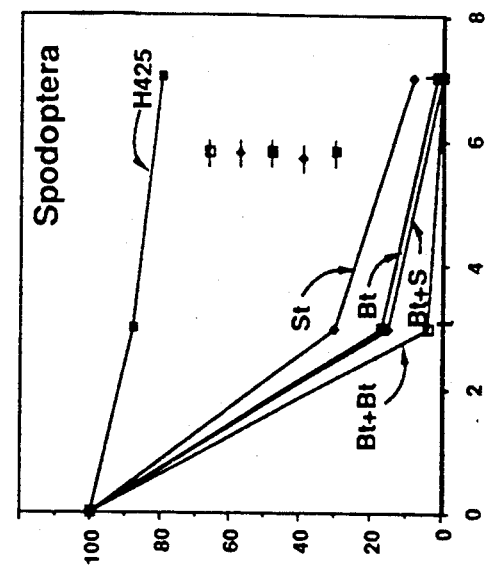
FIG. 9 is a graphical representation of insect feeding trials conducted with transgenic plants.
Figure 9B:
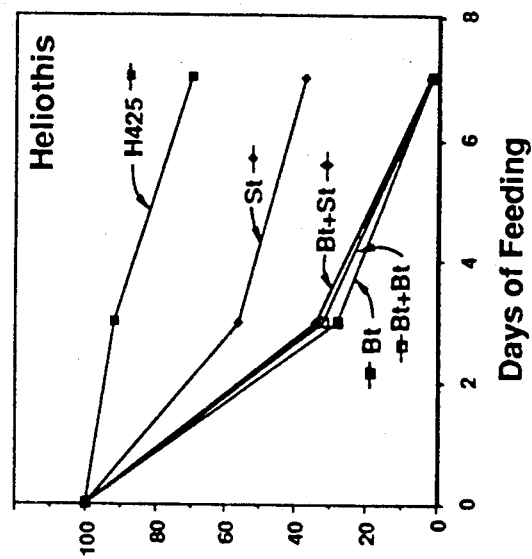
Figure 9A:
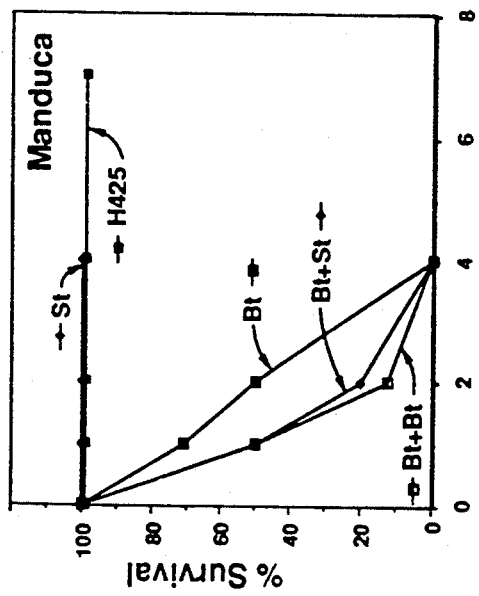

Continued feeding trials with tobacco hornworms on tissues of R1 and R2 plants resulted in no mortality to the insects and insignificant reduction in feeding, relative to controls. However, insect toxicity assays were also conducted with other candidate insects and the results are illustrated in FIG. 9. In particular, insect toxicity studies were conducted with the cotton bollworm (*Heliothis zea*) and the beet armyworm (*Spodoptera exigua*). When supplied tissue from the R1 and R2 progeny of plant T2636, both bollworms and armyworms were each subject to very high mortality and dramatically reduced feeding behaviors. The same findings were found on other plants which were the progeny of original R0 plants which had previously been determined to express lower levels of the AaIT transcripts than the plant T2636.

To verify the effect of the AaIT peptide on target insects, separately from the peptide produced in the plant cells, the commercially available preparation of crude venom of *Androctonus australis* (Sigma Chemical) was introduced both through topical and ingested applications. For topical use, the AaIT peptide was dissolved in 50% DMSO at a concentration of approximately 5 milligrams per milliliter, and approximately 1 microliter of this solution was directly applied to the skin of the target insect. Paralysis, behavior modifications, and mortality relative to the controlled treatments were monitored for up to 24 hours following application. It was discovered that the toxin is active if topically applied to hornworms, even though it seemed relatively ineffective in an ingested form in plant tissues. Reduced activity of treated hornworm larvae, as well as occasional spastic responses, were observed for periods of time after topical application, generally followed by complete recovery. Injection of toxin resulted in a prolonged period of reduced activity, but not in mortality. Other organisms, such as the cotton bollworm, were sensitive to the toxin whether the root of introduction was topical application, injection, or ingestion.

FIG. 9 summarizes the feeding trial of the various insect larvae on the progeny of tobacco plant T3376, an R1 progeny of the primary R0 regenerate plant T2636. To generate the plants used for the tests summarized in FIG. 9, the plant T3376 was propagated in three ways, by self-pollination, by out crossing as either a pollen donor or a maternal pollen recipient to plant T3219, an R2 plant which had within it a homozygous insertion of the single BTS gene expressing the Bacillus thuringiensis delta-endotoxin in insect toxic doses, and in addition plant T3219 was self-pollinated. Prior to feeding trials all of the progeny of these crosses were analyzed by polymerase chain reaction (PCR) to confirm the presence of the appropriate AaIT or B.t. sequences. Self progeny of the plant T3219 were expected to be homozygous B:t., while outcrosses of T3219 and T3376 have been isolated which contained a single copy of both of the relevant genes. Progeny of plant T3376, which did not contain an AaIT gene, were excluded from the study.

In the graphs of FIG. 9, "St" represents larvae fed tissues from the self-pollinated progeny of plant T2636, "H425" represents larvae fed wild-type (nontransgenic) Havana 425 tobacco tissues as a control, "Bt" represents larvae fed tissues of plants apparently heterozygous with a single copy of B.t. gene (resulting from crossing of T3219 with T3376), "B.t.+B.t." represents larvae fed tissues from apparently homozygous B.t. gene-containing tobacco plants (from self-pollinated T3219), while "B.t.+S.t." represents larvae fed tissues of plants derived from crosses between a B.t. gene containing parent (T3219) and a parent containing an AaIT gene (T3376). The three graphs show survival of Manduca sexta, Heliothis and Spodoptera over 0-8 days feeding on such tissues. It can be seen that the AaIT gene had no obvious effect on Manduca in this experiment, but AaIT caused significant mortality relative to controls to both Heliothis and Spodoptera. Furthermore, the presence of both B.t. and AaIT in a plant provides at least as much toxicity to insects as either toxin individually, and a possible additive effect is indicated. Thus, the presence of both toxins would be expected to serve as a deterent to the development of resistance to either individual toxin.

The studies revealed that the chimeric genetic construction is stable through at least the R2 generation and that the toxicity to susceptible insects continues and is an inheritable trait which can be passed to progeny plants by Mendelian inheritance. This observation is consistent with previous experiments in the insertion of transgenic genes into the germ line of plants.

EXAMPLE 2

An insecticidal polypeptide possessing neurotoxic activity toward insects (Insectotoxin I1, or BeIT1) was isolated from the venom of the Central Asian scorpion Buthus epeus Zhdanova et al., Bioorganicheskaya Khimiya, 3 pp. 485-493 (1977), Grishin, Int. J. Quant. Chem., 19, pp. 291-298 (1981). Following purification of the peptide and tests for bioactivity, amino acid sequence was obtained and shown to be (in single letter amino acid code):

MCMPCFTTRPDMAQQCRACCKGRGKCFGPQCLCGYD

As in Example 1 demonstrating synthesis of a gene encoding the AaIT peptide, a chimeric gene was constructed to enable expression of BeIT1 in plants including a synthetic coding region. Based on the most frequently used codons in plants (FIG. 1), four oligonucleotides designated MM83 through MM86 were synthesized to span the amino acid coding region of the peptide. Illustrated in FIG. 5 is both the synthetic coding region and the oligonucleotides. Oligonucleotides MM83 and MM85 are complimentary, and represent the amino-terminal portion of the peptide coding sequence. Oligonucleotides MM84 and MM86 are complimentary, representing the carboxyl-terminal portion of the coding region. To construct the functional gene for expression in plants, the four synthetic oligonucleotides were initially combined in complimentary pairs and annealed, then the two sets of pairs were combined and the overlaps annealed. The oligonucleotides were then treated with polynucleotide kinase in the presence of ATP to provide 5'-monophosphates at the hydroxyl termini of the oligonucleotides to facilitate ligation. The annealed oligonucleotides were then combined with pUC18 plasmid vector previously digested with Hind III and Bam HI. DNA ligase was then provided to ligate the pairs together, and to join the synthetic BeIT1 coding region to the vector pUC18. E. coli was transformed to ampicillin resistance, and appropriate plasmids were identified by DNA minipreps. The insert DNA was sequenced to confirm the sequence as shown in FIG. 5.

As may be seen by reference to FIG. 5, the 5' end of the duplex oligonucleotide has a four nucleotide sticky end (overlap) compatible with that generated by the endonuclease Hind III, while the 3' end has a sticky end compatible with that generated by endonuclease Bam HI. Immediately adjacent to the Hind III site in the synthetic insert is a recognition site for cleavage with BspMI, an endonuclease that cleaves distally from the hexanucleotide recognition site, which in this oligonucleotide will result in a 4-nucleotide sticky end compatible with that of endonuclease Nco I. Nco I is the enzyme recognition site that will be used to join the BeIT1 coding sequence to regulatory DNA sequence from pAMVBTS for construction of the functional chimeric gene, where the central "ATG" in the Nco I recognition "CCATGG" will represent the first codon of the BeIT1 coding sequence. Because the second codon of BeIT1 is cystine (Cys, TGC) it is not possible to provide an Nco I cleavage site, since that would require that the first nucleotide of the codon be a "G" (to complete the Nco I recognition sequence CCATGG). BspMI was therefore used on the BeIT fragment to generate the compatible "CATG" sticky end, which will ligate to Nco I generated sites, although the Nco I recognition site will be destroyed by the ligation. At the carboxy-terminus of the coding region, immediately adjacent to the Bam HI site, is a recognition sequence for Pst I (CTGCAG), the enzyme used to excise the coding sequence from pUC18 for ligation of the carboxy-terminus into the expression plasmid for chimeric gene construction.

Figure 6:
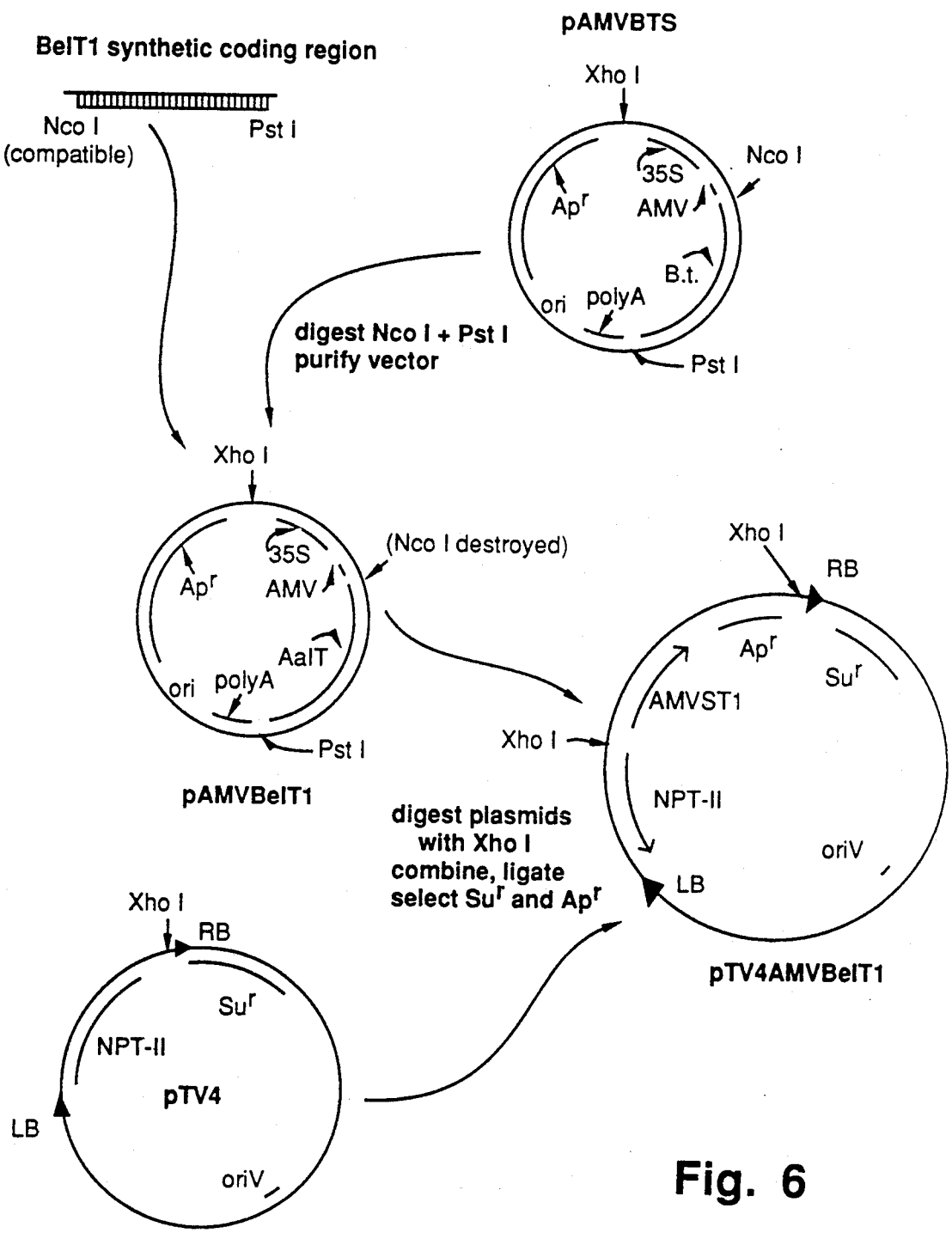
FIG. 6 is a schematic illustration of the construction of pTV4AMVBeIT1.

As illustrated in FIG. 6, to construct a chimeric gene capable of expression in plants, the plasmid pAMVBTS was digested to completion with enzymes Nco I and Pst I, and the vector was purified from agarose gels following electrophoresis. The BspMI and Pst I digested oligonucleotide encoding BeIT1 was purified from pUC18 in a similar manner, the two DNA fragments were combined and ligated. E. coli was transformed and selected for ampicillin resistance, and the properly constructed plasmid pAMVBeIT1 was identified by minipreps. This plasmid is essentially identical to pAMVST1, except for the different amino acid coding regions specifying the two different insect toxins. From 5' to 3', the expression cassette consists of the CaMV 35S promoter, the mRNA 5' noncoding translational enhancer region corresponding to that of alfalfa mosaic virus coat protein mRNA, the synthetic coding sequence for BeIT1, and the polyadenylation region from nopaline synthase.

In order to move pAMVBeIT1 into plant cells, the plasmid was digested at a unique Xho I endonuclease site immediately 5' to the CaMV 35S promoter, and the plasmid was cointegrated by ligation with Xho I digested Agrobacterium vector plasmid pTV4. Following transformation of E. coli, and selection for both sulfadiazene and ampicillin resistance, the properly cointegrated plasmids to pTV4AMVBeIT1 were identified by DNA minipreps. These plasmids were then conjugated into Agrobacterium and used in transformation of plant tissues as described previously in Example 1 and Barton et al. (Barton, Whiteley and Yang).

Following regeneration of plants transformed with AMVBeIT1, approximately 50 plants will be screened using mRNA slot-blots to identify those plants that express the BeIT1 gene most strongly. The four plants with the most BeIT1 mRNA will be allowed to flower and set seed, and the progeny will be analyzed in insect feeding trials. As with AaIT, toxicity is expected to be present against some species of insects. In addition to self-pollination of plants containing BeIT1, the four plants with highest expression will be outcrossed to plants previously identified to express significant levels of either AaIT (Example 1), B.t. delta-endotoxin, or BeIT2 (Example 3). Progeny of these outcrosses will be subjected to insect toxicity bioassays, and it is expected that each toxin activity will be functional in the progeny and further that additive effects will be apparent between some of the toxins, resulting in additional levels of insect resistance. It is expected that the development of resistance to these toxins by susceptible insects is significantly delayed by the presence of two different toxins within the same plant.

EXAMPLE 3

An insecticidal polypeptide (Insectotoxin I2, or BeIT2) possessing neurotoxic paralytic activity toward insects has been isolated from the venom of the Central Asian scorpion *Buthus epeus* Grishin et al., *Bioorganicheskaya Khimiya*, 5, pp. 1285-1294 (1979); Grishin, *Int. J. Quant. Chem.*, 19, pp. 291-298 (1981). Following purification of the peptide and tests for bioactivity, amino acid sequence was obtained and shown to be (in single letter amino acid code):

MADGYVKGKSGCKISCFLDNDLCNADCKYYGGKLN
SWCIPDKSGYCWCPNKGWNSIKSETNTC

Figure 7:
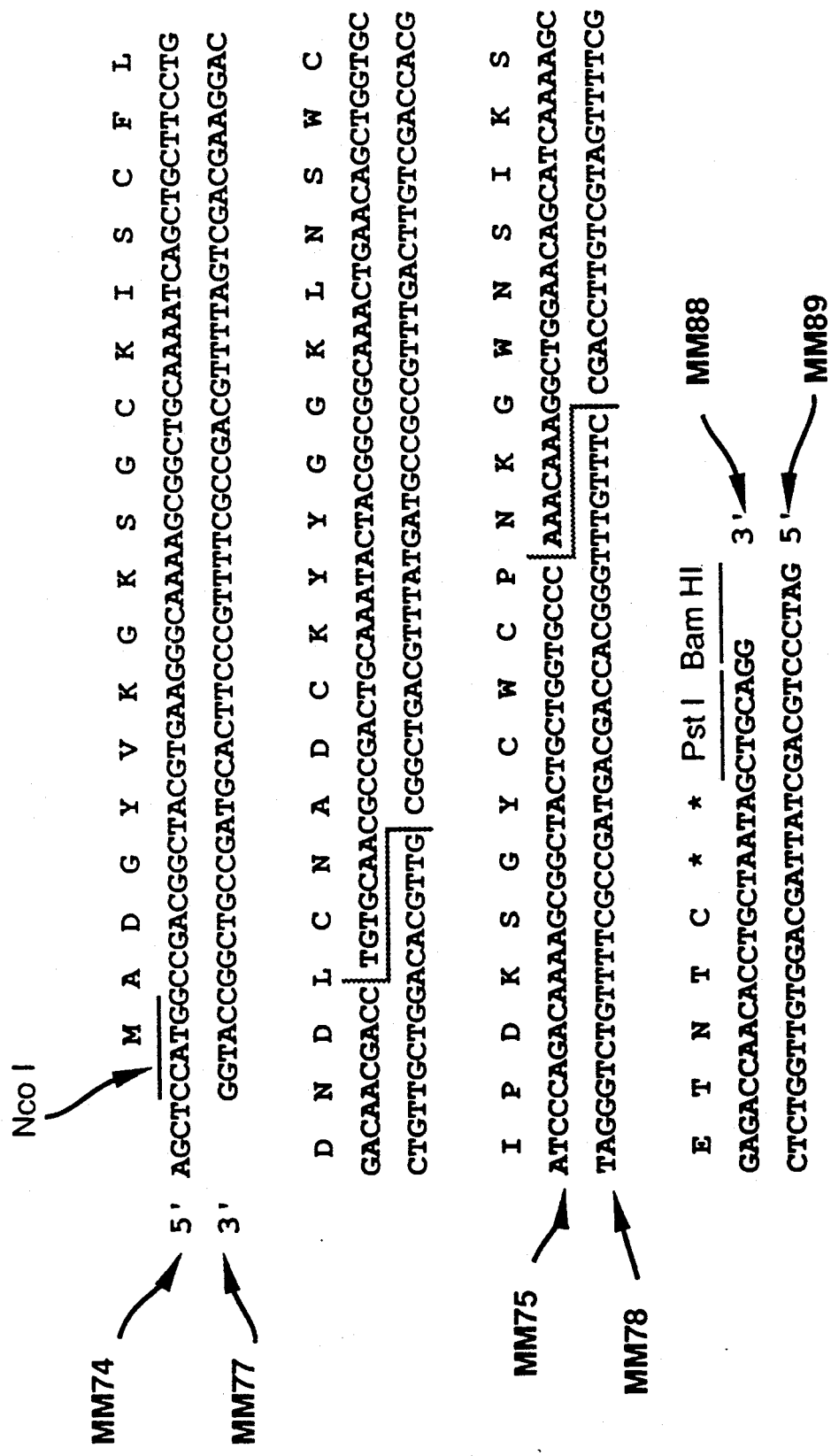
FIG. 7 is a sequence listing of the synthetic coding region for the BeIT2 toxin and the oligonucleotides used to construct it.

As in Examples 1 and 2 demonstrating synthesis of genes encoding the AaIT and BeIT1 peptides, respectively, a chimeric toxin gene was constructed to enable expression of BeIT2 in plants. Based on the most frequently used codons in plants (FIG. 1), six oligonucleotides were synthesized to span the amino acid coding region of the peptide. These oligonucleotides, as they anneal to form the complete coding sequence, are shown in FIG. 7. Oligonucleotides MM74 and MM77, MM75 and MM78, and MM88 and MM89 are complimentary pairs, and represent the amino-terminal portion, the central portion, and the carboxy-terminal portion of the synthetic BeIT2 coding sequence. To construct the functional gene for expression in plants, the six synthetic oligonucleotides were initially combined in 3 separate reactions as complimentary pairs and then annealed. The reaction containing the central pair of oligonucleotides (MM75 and MM78) was then treated with polynucleotide kinase in the presence of ATP to provide 5'-monophosphates at the hydroxyl termini of these two oligonucleotides, to facilitate ligation to the other two pairs. The three pairs of annealed oligonucleotides were then combined into one reaction, which included pUC18 (previously digested with Hind III and Bam HI), and the overlaps were allowed to anneal. DNA ligase was then provided to ligate the three pairs together, and to insert the synthetic BeIT2 coding sequence into the pUC18 vector. E. coli was transformed and selected for ampicillin resistance, and appropriate plasmids were identified by DNA minipreps. The insert DNA was sequenced to confirm the sequence as shown in FIG. 7.

The 5' end of the complete oligonucleotide for BeIT2, as shown in FIG. 7, had a sticky end (overlap) compatible with that generated by the endonuclease Hind III, although this site was destroyed in ligation to the pUC18 vector. The 3' end of the synthetic DNA has a sticky end compatible with that generated by endonuclease Bam HI, with this site retained in the pUC-derived plasmid. Immediately adjacent to the Hind III-compatible site in the synthetic insert is a recognition site for endonuclease Nco I. This is the enzyme recognition site that was used to join the BeIT2 coding sequence to regulatory DNA sequences derived from pAMVBTS for construction of the functional chimeric gene, where the central "ATG" in the Nco I recognition sequence "CCATGG" will represent the first codon of the BeIT2 coding sequence. At the carboxy-terminus of the coding region, between Bam HI site and the termination codons is a recognition sequence for Pst I (CTGCAG), the enzyme used to excise the coding sequence from pUC18 for ligation of the carboxy-terminus into the expression plasmid for chimeric gene construction.

Figure 8:
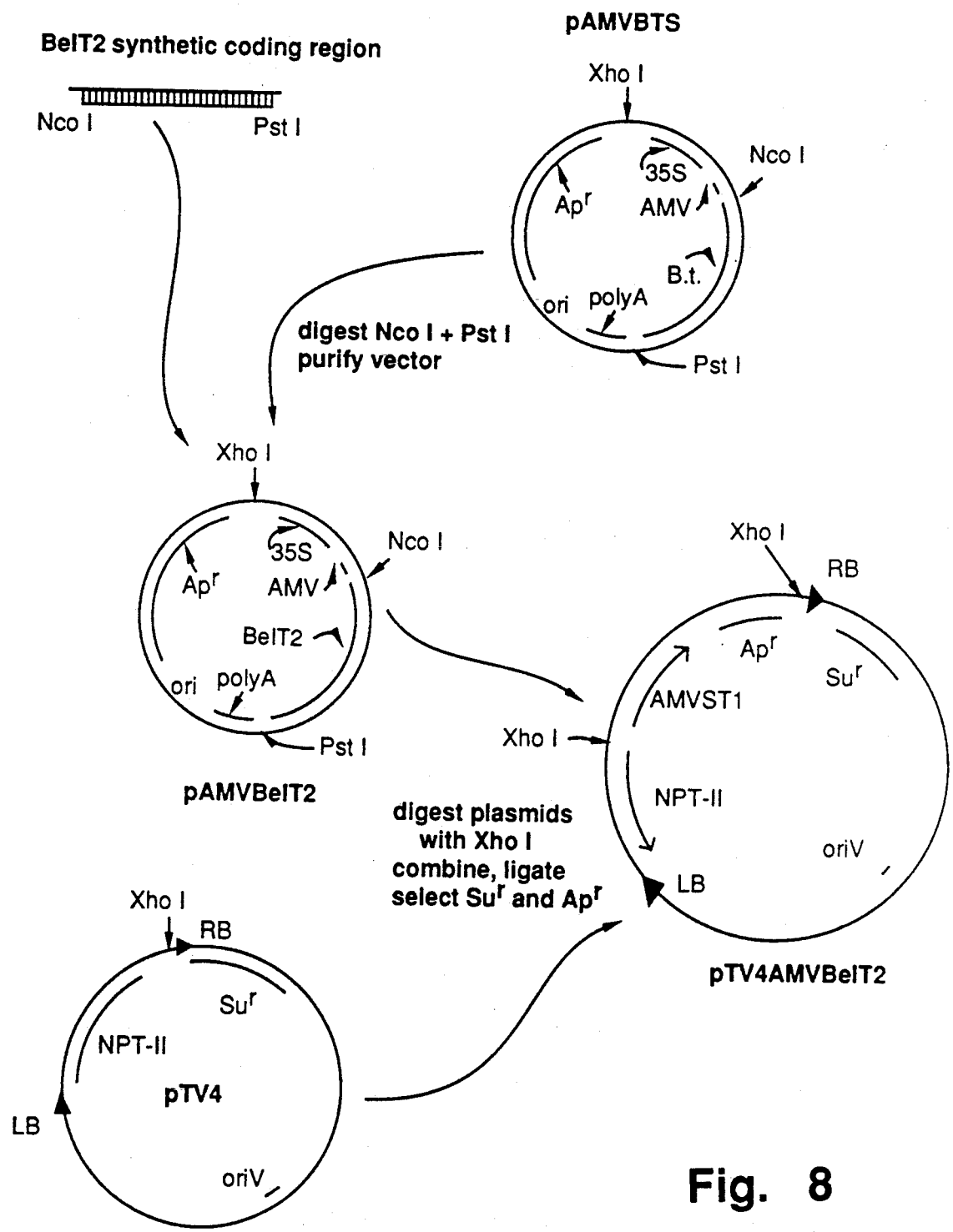
FIG. 8 is a schematic illustration of the construction of pTV4AMVBeIT2.

As shown in FIG. 8, to construct a chimeric gene capable of expression in plants, the plasmid pAMVBTS was digested to completion with enzymes Nco I and Pst I, and the vector was purified from agarose gels following electrophoresis. The Nco I and Pst I digested duplex oligonucleotide encoding BeIT2 was purified from pUC18 in a similar manner, after which the two DNA fragments were combined and ligated. E. coli was transformed and selected for ampicillin resistance, and the properly constructed plasmid pAMVBeIT2 was identified by minipreps. This plasmid is essentially identical to pAMVST1, except for the different amino acid coding regions specifying the different insecticidal toxins. From 5' to 3', the expression cassette consists of the CaMV 35S promoter, the mRNA 5'-noncoding translational enhancer region corresponding to that of alfalfa mosaic virus coat protein mRNA, the synthetic coding sequence for BeIT2, and the polyadenylation region from nopaline synthase.

In order to move pAMVBeIT2 into plant cells, the plasmid was digested at a unique Xho I endonuclease site immediately 5' to the CaMV promoter, and the plasmid was cointegrated by ligation with DNA of Xho I digested Agrobacterium vector plasmid pTV4 by the method of Barton, et al. as described in Example 1. Following transformation of *E. coli* and selection for both sulfadiazene and ampicillin resistance, the properly cointegrated plasmids pTV4AMVBeIT2 were identified by DNA minipreps. These plasmids were then conjugated into Agrobacterium and used in transformation of plant tissues as described previously in Example 1 and Barton et al.

Following regeneration of plants transformed with pTV4AMVBeIT2, approximately 50 plants will be screened using mRNA slot-blots to identify those plants that express the BeIT2 gene most strongly. The four plants with the most BeIT2 mRNA will be allowed to flower and set seed, and the progeny will be analyzed in insect feeding trials. As with AaIT, toxicity will be present against some species of insects. In addition to self-pollination, the four plants with highest expression of BeIT2 genes will be outcrossed to plants previously identified to express significant levels of either AaIT peptide, *B.t.* delta-endotoxin, or BeIT1 peptide (Example 2). Progeny of these outcrosses will be subjected to bioassays, and it is expected that each independent toxin activity will be functional in the progeny, and further that additive effects will be apparent between some of the toxins resulting in additional levels of insect resistance. It is expected that in subsequent experiments that the development of resistance to these toxins by susceptible insects will be significantly delayed by the presence of two different toxins within the same plant.

EXAMPLE 4

A series of insecticidal polypeptides possessing neurotoxic activity toward insects (agatoxins I through VI) were isolated from the venom of the funnel web spider, *Agelenopsis aperta* Skinner et al., *J. Biol. Chem.*, 264, pp. 2150-2155 (1989). Following purification of the peptide and tests for bioactivity, amino acid sequences were obtained for each of the six peptides, which were found to be highly homologous. The amino acid sequence for agatoxin IV (AgaIV), which was demonstrated to be insecticidal when injected into several insect species, is shown below: (in single letter amino acid code):

ACVGENQQCADWAGPHCCDGYYCTCRYFPKCICRNNN

Figure 10:
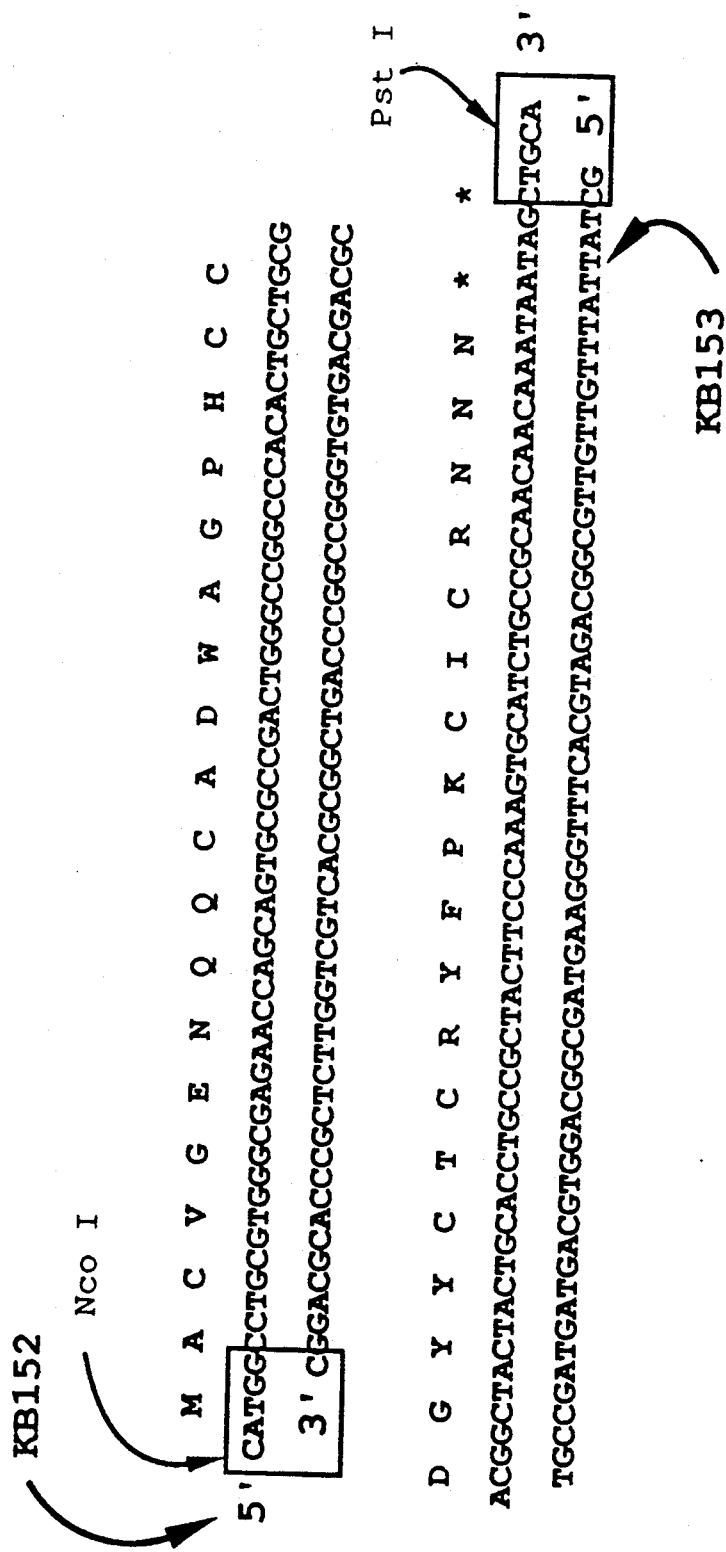
FIG. 10 is a sequence listing of the synthetic coding region for the AgaIV toxin and the oligonucleotides to construct it.
Figure 11:
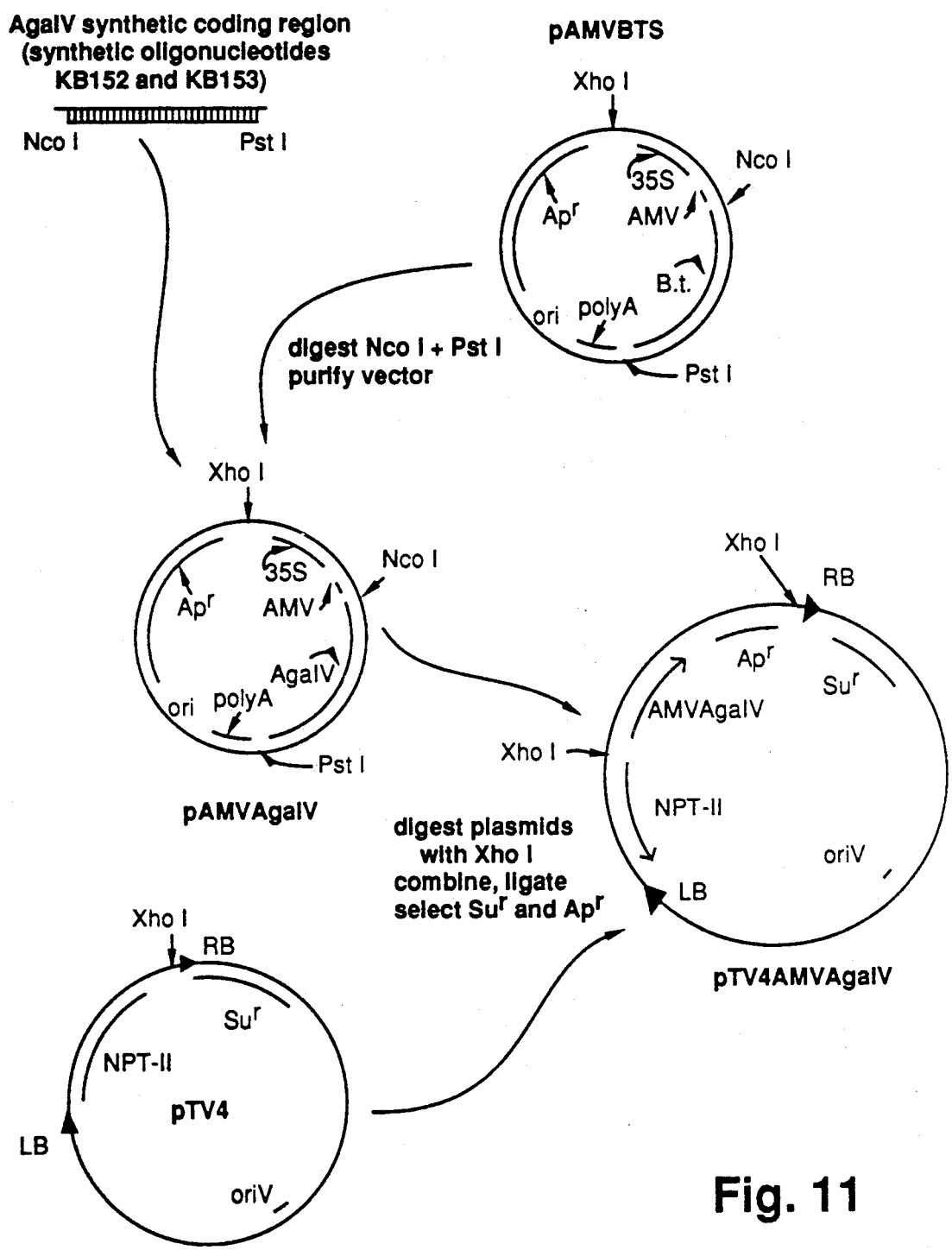
FIG. 11 is a schematic illustration of the construction of pTV4AMVAgaIV.

As in Example 1 demonstrating synthesis of a gene encoding the AaIT peptide, a gene may be constructed to enable expression of AgaIV in plants. Based on the most frequently used codons in plants (FIG. 1), two complimentary oligonucleotides (KB152 and KB153) may be synthesized to span the amino acid coding region of the peptide. The synthetic nucleotide sequence to express the AgaIV toxin is shown in FIG. 10. The manipulations for constructing a gene for expression in plants and transfer of that gene into plant cells are shown in FIG. 11. To construct the functional gene for expression in plants, the 2 synthetic oligonucleotides are initially combined in one reaction and annealed. This generates a duplex oligonucleotide with Nco I and Pst I compatible ends at the amino-terminal and carboxy-terminal ends of the coding sequence, respectively. In a separate reaction, the plasmid pAMVBTS may be digested to completion with enzymes Nco I and Pst I, and the vector may be purified from agarose gels following electrophoresis. The annealed oligonucleotides encoding AgaIV can then be combined with the pAMVBTS vector fragment, and DNA ligase added to ligate the vector and coding region together. *E. coli* may be transformed to ampicillin resistance and appropriate plasmid, pAMVAgaIV, can be identified by DNA minipreps. The insert DNA may be sequenced to confirm the sequence as shown in FIG. 10. From 5' to 3', the expression cassette would consist of the CaMV 35S promoter, the mRNA 5' noncoding region corresponding to that of alfalfa mosaic virus coat protein mRNA, the synthetic coding sequence for AgaIV, and the polyadenylation region from nopaline synthase.

In order to move pAMVAgaIV into plant cells, the plasmid can be digested at a unique Xho I endonuclease site immediately 5' to the CaMV 35S promoter, and the plasmid can be cointegrated by ligation with Xho I digested Agrobacterium vector plasmid pTV4. Following transformation of *E. coli* and selection for both sulfadiazene and ampicillin resistance, the properly cointegrated plasmids pTV4AMVAgaIV can be identified by DNA minipreps. These plasmids can be then conjugated into Agrobacterium and used in transformation of plant tissues as described previously in Example 1 and Barton et al., supra.

Following regeneration of plants transformed with AMVAgaIV, approximately 50 plants are to be screened using mRNA slot-blots to identify those plants that express the AgaIV gene most strongly. The four plants with the most AgaIV mRNA can be allowed to flower and set seed, and the progeny analyzed in insect feeding trials. As with AaIT, toxicity is expected against some species of insects. In addition to self-pollination of plants containing AgaIV, the four plants with highest expression can be outcrossed to plants previously identified to express significant levels of either AaIT (Example 1), *B.t.* delta-endotoxin, BeIT1 (Example 2), BeIT2 (Example 3) or other insecticidal toxins. Progeny of these outcrosses may be subjected to bioassays, and it may be observed that each toxin activity was functional in the progeny and further that additive effects are apparent between some of the toxins, resulting in additional levels of insect resistance. It may be found in subsequent experiments that the development of resistance to these toxins by susceptible insects was significantly delayed by the presence of two different toxins within the same plant.

EXAMPLE 5

An insecticidal polypeptide possessing neurotoxic activity toward insects (termed in this example as "SfIT") was isolated from the venom of the cellular spider, *Segestria florentina*, Sagdiev et al., *Bioorganicheskaya Khimiya*, 13, pp. 1013-1018 (1987). Following purification of the peptide and tests for bioactivity, amino acid sequence was obtained. The amino acid sequence for SfIT, which has a molecular mass of 3988 daltons, and is comprised of 35 amino acids, (excluding an amino-terminal methionine which is added in the example below), is shown below in single letter amino acid code:

RQDMVDESVCYITDNNCNGGKCLRSKACHADPWEL

Figure 12:
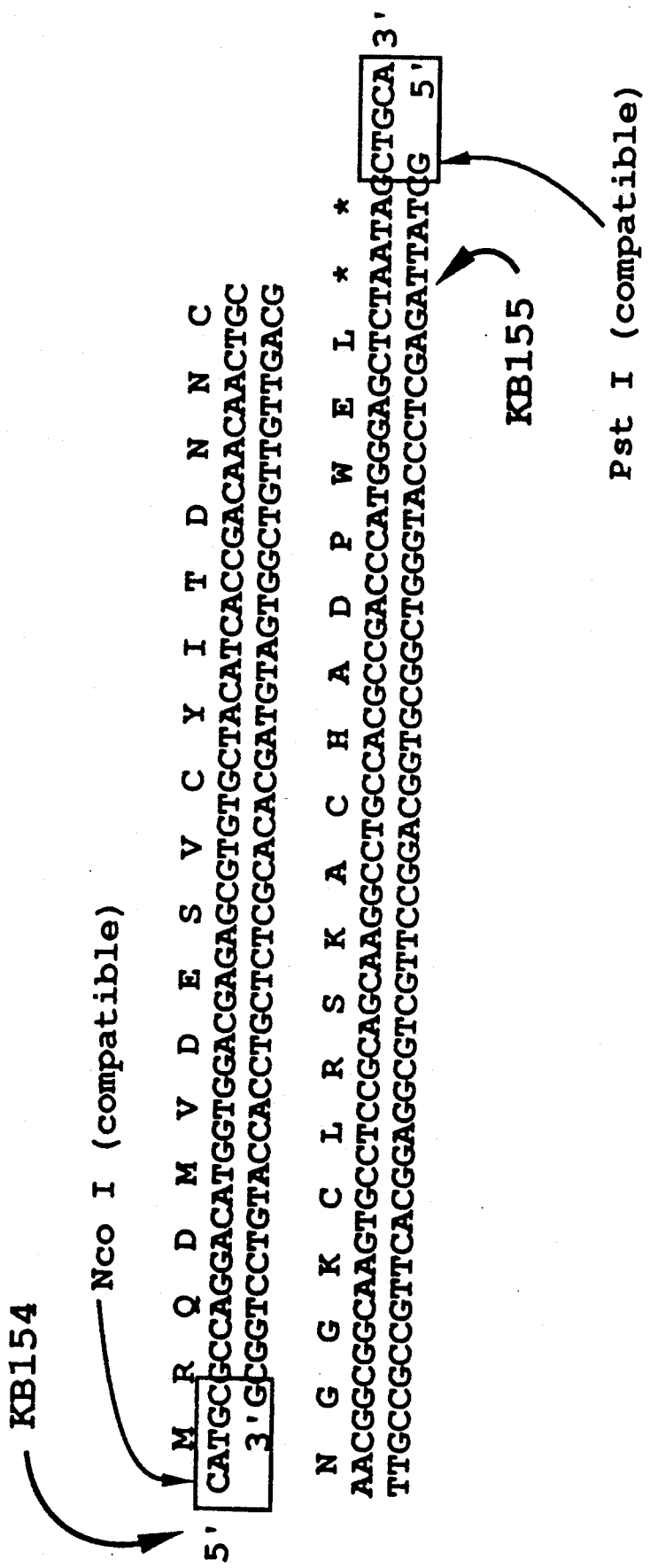
FIG. 12 is a sequence listing of the synthetic coding region for the SfIT toxin and the oligonucleotides to construct it.

As in Example 1 demonstrating synthesis of a gene encoding the AaIT peptide, a chimeric gene can be constructed to enable expression of SfIT in plants. Based on the most frequently used codons in plants (FIG. 1), two complimentary oligonucleotides (KB154 and KB155) can be synthesized to span the amino acid coding region of the peptide; an additional codon for methionine, ATG, is included at the amino-terminus of the coding region to enable appropriate translational initiation (FIG. 12). The manipulations of these oligonucleotides to construct an expression cassette and transfer it into plants are illustrated in FIG. 13. To construct the functional gene for expression in plants, the two synthetic oligonucleotides can be initially combined in one reaction and annealed. This generates a duplex oligonucleotide with Nco I and Pst I compatible ends at the amino-terminal and carboxy-terminal ends of the coding sequence, respectively. In a separate reaction, the plasmid pAMVBTS can be digested to completion with enzymes Nco I and Pst I, and the vector can be purified from agarose gels following electrophoresis. The annealed oligonucleotides encoding SfIT can then be combined with the pAMVBTS vector fragment, and the DNA ligase can be added to ligate the vector and coding region together. E. coli can be transformed and selected for ampicillin resistance, and appropriate plasmids, pAMVSfIT, containing expression cassettes can be identified by DNA minipreps. The insert DNA would be sequenced to confirm the sequence as shown in FIG. 12. From 5' to 3', the expression cassette consists of the CaMV 35S promoter, then the mRNA 5' noncoding region corresponding to that of alfalfa mosaic virus coat protein mRNA, the synthetic coding sequence for SfIT, and the polyadenylation region from nopaline synthase.

In order to move pAMVSfIT into plant cells, the plasmid may be digested at a unique Xho I endonuclease site immediately 5' to the CaMV 35S promoter, and the plasmid may be cointegrated by ligation with Xho I digested Agrobacterium vector plasmid pTV4. Following transformation of E. coli and selection for both sulfadiazene and ampicillin resistance, the properly cointegrated plasmids pTV4AMVSfIT can be identified by DNA minipreps. These plasmids may then be conjugated into Agrobacterium and used in transformation of plant tissues as described previously in Example 1 and Barton et al., supra.

Following regeneration of plants transformed with AMVSfIT, approximately 50 plants are screened using mRNA slot-blots to identify those plants that express the SfIT gene most strongly. The four plants with the most SfIT mRNA can be allowed to flower and set seed, and the progeny analyzed in insect feeding trials. As with AaIT, toxicity is expected to be present against some species of insects. In addition to self-pollination of plants containing SfIT, the four plants with highest expression can be outcrossed to plants previously identified to express significant levels of either AaIT (Example 1), B.t delta-endotoxin, BeIT1 (Example 2), BeIT2 (Example 3) or other insecticidal toxins. Progeny of these outcrosses may be subjected to bioassays, and it will be observed that each toxin activity is functional in the progeny and further that additive effects are apparent between some of the toxins, resulting in additional levels of insect resistance. It would be apparent in subsequent experiments that the development of resistance to these toxins by susceptible insects is significantly delayed by the presence of two different toxins within the same plant.

We claim:

1. A dicot plant comprising in its genome an inheritable genetic construction including a promoter effective to promote expression of a downstream coding sequence in plant cells, a coding region coding for the expression in plant cells of insect specific toxin AaIT, and a termination sequence effective to terminate the transcription or translation of the genetic construction in plant cells, the genetic construction effective to express in the cells of the plant sufficient amounts of AaIT to be lethal upon ingestion by *Heliothis zea*.

2. A dicot plant comprising in its genome two linked inheritable genetic constructions, each including a promoter effective to promote expression of a downstream coding sequence in plant cells, and a termination sequence effective to terminate the transcription or translation of the genetic construction in plant cells, one genetic construction including a coding region coding for the expression in plant cells of insect specific toxin AaIT, the other genetic construction including a coding region coding for the expression in plant cells of the Lepidopteran specific delta endotoxin gene from *Bacillus thuringiensis*, the linked genetic constructions effective to express in the cells of the plant sufficient amounts of AaIT to be lethal upon ingestion by *Heliothis zea* and sufficient amounts of the delta endotoxin to be toxic upon ingestion by *Manduca sexta*.

* * * * *